US010365565B2

(12) United States Patent
Pandey et al.

(10) Patent No.: US 10,365,565 B2
(45) Date of Patent: Jul. 30, 2019

(54) METHOD OF MEASURING A STRUCTURE, INSPECTION APPARATUS, LITHOGRAPHIC SYSTEM, DEVICE MANUFACTURING METHOD AND WAVELENGTH-SELECTIVE FILTER FOR USE THEREIN

(71) Applicant: ASML Netherlands B.V., Veldhoven (NL)

(72) Inventors: Nitesh Pandey, Eindhoven (NL); Arie Jeffrey Den Boef, Waalre (NL); Marinus Johannes Maria Van Dam, Venlo (NL)

(73) Assignee: ASML Netherlands B.V., Veldhoven (NL)

( * ) Notice: Subject to any disclaimer, the term of this patent is extended or adjusted under 35 U.S.C. 154(b) by 48 days.

(21) Appl. No.: 15/435,593

(22) Filed: Feb. 17, 2017

(65) Prior Publication Data
US 2017/0242343 A1 Aug. 24, 2017

(30) Foreign Application Priority Data
Feb. 19, 2016 (EP) .................................. 16156466

(51) Int. Cl.
*G03B 27/72* (2006.01)
*G03F 7/20* (2006.01)
(Continued)

(52) U.S. Cl.
CPC ..... *G03F 7/70191* (2013.01); *G01N 21/4788* (2013.01); *G02B 5/22* (2013.01);
(Continued)

(58) Field of Classification Search
CPC ............ G03F 7/70133; G03F 7/70191; G03F 7/70616; G03F 7/70625;
(Continued)

(56) References Cited

U.S. PATENT DOCUMENTS 5,596,406 A 1/1997 Rosencwaig et al.
5,596,411 A 1/1997 Fanton et al.
(Continued)

FOREIGN PATENT DOCUMENTS

CN 101299132 A 11/2008
CN 104483817 A 4/2015
(Continued)

OTHER PUBLICATIONS

Machine translation of CN 101299132 A, dated Nov. 5, 2008.*
(Continued)

*Primary Examiner* — Peter B Kim
(74) *Attorney, Agent, or Firm* — Sterne, Kessler, Goldstein & Fox P.L.L.C.

(57) ABSTRACT

A scatterometer performs diffraction based measurements of one or more parameters of a target structure. To make two-color measurements in parallel, the structure is illuminated simultaneously with first radiation (302) having a first wavelength and a first angular distribution and with second radiation (304) having a second wavelength and a second angular distribution. The collection path (CP) includes a segmented wavelength-selective filter (21, 310) arranged to transmit wanted higher order portions of the diffracted first radiation (302X, 302Y) and of the diffracted second radiation (304X, 304Y), while simultaneously blocking zero order portions (302", 304") of both the first radiation and second radiation. The illumination path (IP) in one embodiment includes a matching segmented wavelength-selective filter (13, 300), oriented such that a zero order ray passing through the illumination optical system and the collection optical system will be blocked by one of said filters or the other, depending on its wavelength.

13 Claims, 7 Drawing Sheets

(51) Int. Cl.
*G01N 21/47* (2006.01)
*G02B 5/22* (2006.01)

(52) U.S. Cl.
CPC ...... *G03F 7/70133* (2013.01); *G03F 7/70616* (2013.01); *G03F 7/70625* (2013.01); *G01N 2021/4711* (2013.01); *G01N 2201/063* (2013.01)

(58) Field of Classification Search
CPC ....... G01N 2021/4711; G01N 21/4788; G01N 2201/063; G02B 5/22
See application file for complete search history.

(56) References Cited

U.S. PATENT DOCUMENTS

| | | | |
|---|---|---|---|
| 5,982,489 | A | 11/1999 | Shiraishi |
| 7,248,375 | B2 | 7/2007 | Opsal et al. |
| 2006/0033921 | A1 | 2/2006 | Den Boef et al. |
| 2006/0066855 | A1 | 3/2006 | Boef et al. |
| 2010/0201963 | A1 | 8/2010 | Cramer et al. |
| 2010/0328655 | A1 | 12/2010 | Den Boef |
| 2011/0027704 | A1 | 2/2011 | Cramer et al. |
| 2011/0043791 | A1 | 2/2011 | Smilde et al. |
| 2011/0069292 | A1 | 3/2011 | Den Boef |
| 2011/0102753 | A1 | 5/2011 | Van De Kerkhof et al. |
| 2012/0044470 | A1 | 2/2012 | Smilde et al. |
| 2012/0123581 | A1 | 5/2012 | Smilde et al. |
| 2012/0242970 | A1 | 9/2012 | Smilde et al. |
| 2013/0141730 | A1 | 6/2013 | Quintanilha |
| 2013/0258310 | A1 | 10/2013 | Smilde et al. |
| 2013/0271740 | A1 | 10/2013 | Quintanilha |
| 2014/0285657 | A1 | 9/2014 | Hwang et al. |

FOREIGN PATENT DOCUMENTS

| | | |
|---|---|---|
| WO | WO 2013/178422 A1 | 12/2013 |
| WO | WO 2015/018625 A1 | 2/2015 |
| WO | WO 2016/015734 A1 | 2/2016 |

OTHER PUBLICATIONS

International Search Report and Written Opinion of the International Searching Authority directed to International Application No. PCT/EP2017/052594, dated Apr. 6, 2017; 15 pages.

\* cited by examiner

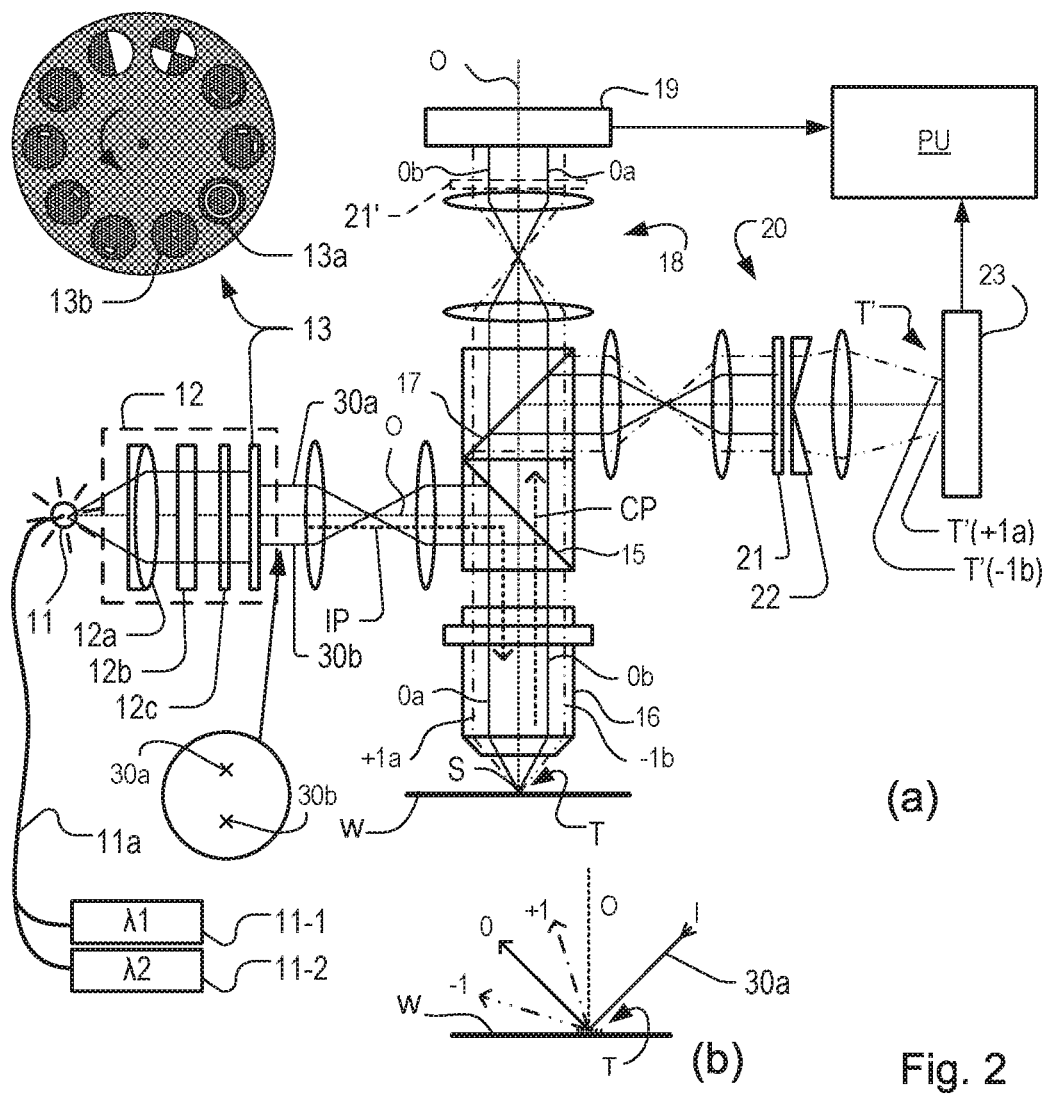
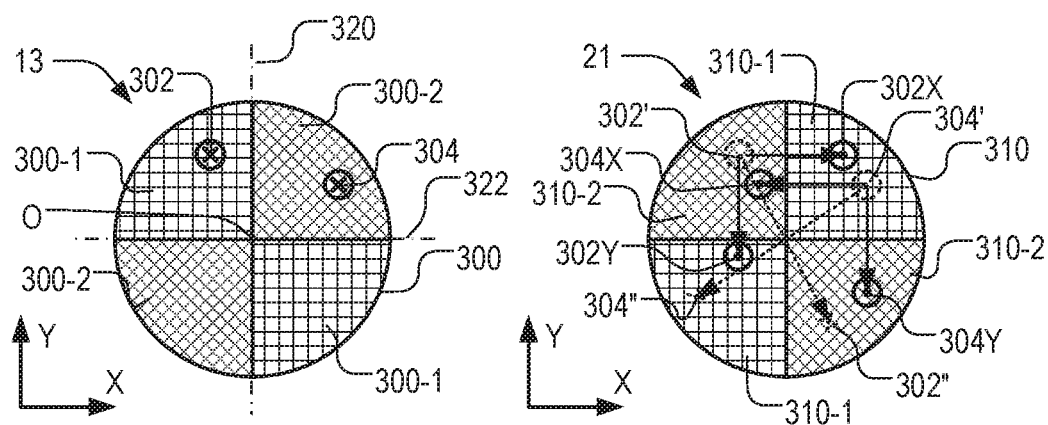
Fig. 2
Fig. 3

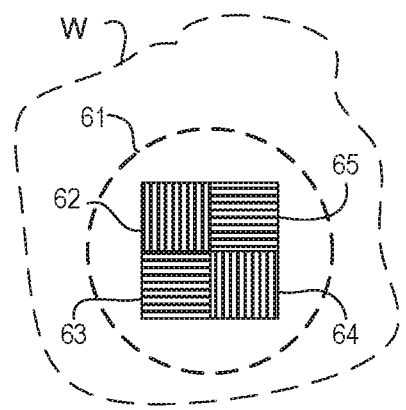
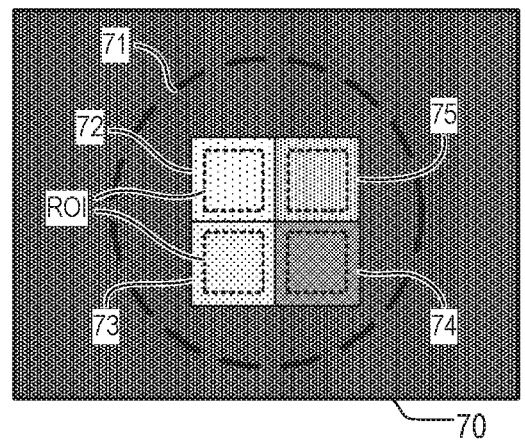
Fig. 6    Fig. 7
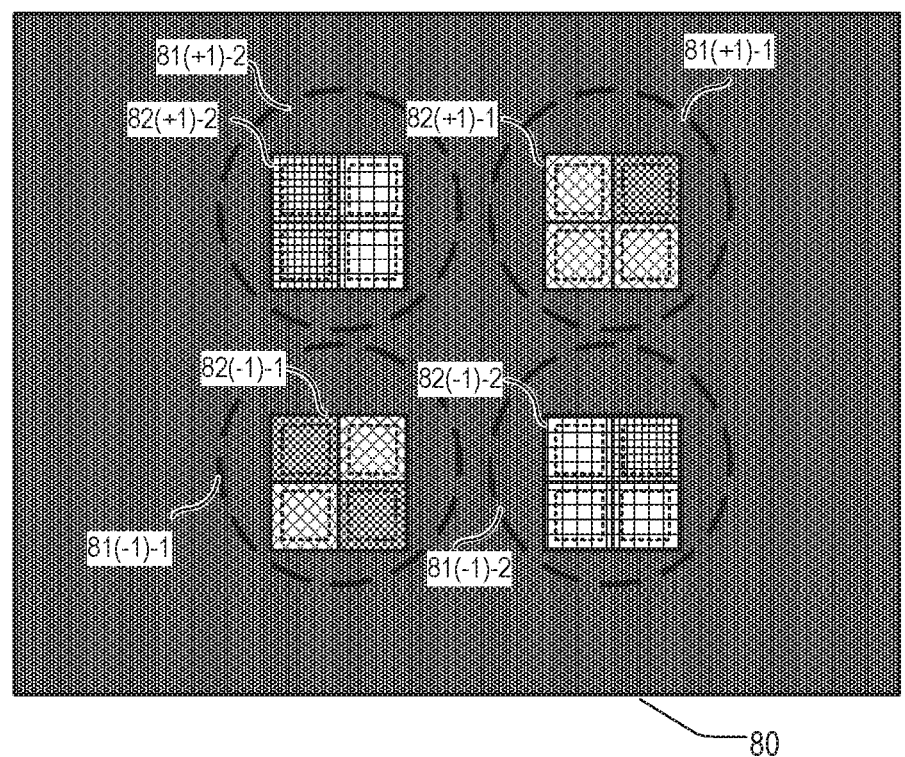
Fig. 8

METHOD OF MEASURING A STRUCTURE, INSPECTION APPARATUS, LITHOGRAPHIC SYSTEM, DEVICE MANUFACTURING METHOD AND WAVELENGTH-SELECTIVE FILTER FOR USE THEREIN

BACKGROUND

Field of the Invention

The present invention relates to methods and apparatus for metrology usable, for example, in the manufacture of devices by lithographic techniques and to methods of manufacturing devices using lithographic techniques. The invention relates in particular to methods and apparatuses for measuring a property of a structure formed by a lithographic process on a substrate.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large gratings, e.g., 40 µm by 40 µm, and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables measurement of overlay and other parameters on smaller targets. These targets can be smaller than the illumination spot and may be surrounded by product structures on a substrate. The intensities that are derived from the adjacent product structures can efficiently be separated from the intensities that are derived from the overlay target with the dark-field detection in the image-plane.

Examples of dark field imaging metrology can be found in patent applications US20100328655A1 and US2011069292A1 which documents are hereby incorporated by reference in their entirety. Further developments of the technique have been described in published patent publications US20110027704A, US20110043791A, US2011102753A1, US20120044470A1, US20120123581A1, US20120242970A1, US20130258310A, US20130271740A and WO2013178422A1. Typically in these methods it is desired to measure asymmetry as a property of the target structure. Targets can be designed so that measurement of asymmetry can be used to obtain measurement of various performance parameters such as overlay, focus or dose. Asymmetry of the structure is measured by detecting differences in intensity between opposite portions of the diffraction spectrum using the scatterometer. For example, the intensities of +1 and −1 diffraction orders may be compared, to obtain a measure of asymmetry.

In these known techniques, appropriate illumination modes and image detection modes are used to obtain the +1 and −1 diffraction orders from periodic structures (gratings) within the target. Each diffraction order may be captured in a separate pupil image or dark-field image, or techniques can be used to capture both +1 and −1 orders in different parts of a single pupil image or dark-field image, which reduces the time penalty associated with each measurement. In the dark-field imaging technique, composite targets comprising multiple gratings can be imaged simultaneously, to allow simultaneous capture of a diffraction order from differently biased gratings in different orientations. Using additionally a number of optical wedge elements as described in US2011102753A1, mentioned above, it is also possible in dark-field imaging to capture both +1 and −1 orders of one or more gratings in a single image. Images of the target using each portion of the diffraction spectrum appear spatially separated on the image sensor. This further reduces the time penalty associated with each measurement of the parameter of interest.

In many cases, the asymmetry signals obtained are dependent to an unknown extent on process variables, not only the performance parameter of interest. In order to improve measurement accuracy of the parameter of interest, it is proposed to measure each target using illuminating radiation of two or more distinct wavelengths. Combining the results from these multiple wavelengths allows process-dependent effects to be distinguished, yielding a more accurate measurement of the parameter of interest. As will be appreciated, however, measurements using two different wavelengths will incur a greater time penalty per target. Therefore in known systems, a trade-off has to be made between measurement accuracy and the number of targets that can be measured during high-volume production.

SUMMARY OF THE INVENTION

The inventors have devised a simple modification of the illumination and detection system, which will allow measurements to be made simultaneously at two wavelengths, with accuracy similar to that of the known measurements. The invention can be applied in angle-resolved scatterometry generally, whether by detection in the pupil plane or by dark-field imaging. Accuracy can be improved over prior published techniques by reducing the influence of process variations.

The invention in a first aspect provides a method of measuring asymmetry in a periodic structure formed by a lithographic process on a substrate, the method comprising the steps of:

(a1) illuminating the structure with first radiation having a first wavelength and a first angular distribution;

(a2) illuminating the structure with second radiation having a second wavelength different to the first wavelength and having a second angular distribution;

(b1) collecting said first radiation after it has been diffracted by the structure;

(b2) collecting said second radiation after it has been diffracted by the structure; and (c) using one or more portions of the diffracted first radiation and the diffracted second radiation to derive a measurement of said property of the structure, wherein the illuminating steps (a1) and (a2) are performed simultaneously, the first angular distribution and the second angular distribution being made different such that the portions of diffracted first radiation that are used in step (c) have an angular distribution that does not overlap with an angular distribution of portions of the diffracted second radiation that are used in step (c), and wherein the collecting steps (b1) and (b2) are performed simultaneously using a collection optical system in which a segmented wavelength-selective filter is arranged to transmit the used portions of the diffracted first radiation and of the diffracted second radiation, while simultaneously blocking one or more other portions of the collected first radiation and second radiation that are not used in step (c).

The invention in some embodiments measures asymmetry in several periodic structures simultaneously, using structures small enough to all fit within a field of view of the measurement optical system. This field of view may be defined for example by an illumination spot size.

In one embodiment, images of multiple gratings for two opposite diffraction orders and for both first and second radiation are all imaged simultaneously at separate locations on an image sensor.

The method may further comprise calculating a performance parameter of said lithographic process based on the asymmetry determined by the method for a plurality of periodic structures. The performance parameter may be for example overlay, focus or dose.

The invention further provides an inspection apparatus configured for measuring asymmetry in a periodic structure on a substrate, the inspection apparatus comprising:

an illumination optical system operable to illuminate the structure simultaneously with first radiation having a first wavelength and a first angular distribution and with second radiation having a second wavelength different to the first wavelength and having a second angular distribution;

a collection optical system operable to collect simultaneously said first radiation after it has been diffracted by the structure and to collect said second radiation after it has been diffracted by the structure; and a processing system for using one or more portions of the diffracted first radiation and the diffracted second radiation to derive a measurement of said property of the structure, wherein the first angular distribution and the second angular distribution are made different such that the portions of diffracted first radiation that are used to derive said measurement have an angular distribution that does not overlap with an angular distribution of portions of the diffracted second radiation that are used to derive said measurement, and wherein the collection optical system includes a segmented wavelength-selective filter arranged to transmit the used portions of the diffracted first radiation and of the diffracted second radiation, while simultaneously blocking one or more other portions of the collected first radiation and second radiation that are not used to derive said measurement.

The facility to measure at two wavelengths simultaneously can be applied in new apparatuses, but also by simple modification of existing optical hardware. Improved measurements can be obtained without the expense of major hardware design and manufacture.

The invention further provides a computer program product comprising machine readable instructions for causing a programmable processing device to implement image processing and calculation steps of a method according to the invention as set forth above. The machine readable instructions may be embodied for example in a non-transitory storage medium.

The invention further provides a lithographic system including a lithographic apparatus and an inspection apparatus according to the invention, as set forth above.

The invention further provides a method of manufacturing devices wherein a device pattern is applied to a series of substrates using a lithographic process, the method including measuring a property of at least one structure formed as part of or beside said device pattern on at least one of said substrates using a method according to the invention as set forth above, and controlling the lithographic process for later substrates based on the result of the asymmetry measurement.

The invention further provides a wavelength-selective filter for use in an optical system, the filter being segmented so as to comprise at least first and second portions, the filter having at least a first pass band in one or more first portions and at least a second pass band in one or more second portions, the first portions transmitting radiation of a first wavelength while blocking radiation of a second wavelength, the second portions transmitting radiation of the second wavelength while blocking radiation of the first wavelength.

The invention yet further provides a pair of such filters.

The invention yet further provides an inspection apparatus having an illumination optical system for providing illumination using at least two wavelengths of radiation, and a collection optical system for collecting radiation having said two wavelengths after interaction with a target structure, wherein at least one of the illumination optical system and the detection optical system includes a segmented wavelength-selective filter according to the invention as set forth above.

In an embodiment of such an inspection apparatus, each of the illumination optical system and the collection optical system includes a segmented wavelength-selective filter device, the segmented wavelength-selective filters of the two optical systems being oriented such that a zero order ray passing through the illumination optical system and the collection optical system will be blocked by one of said filters or the other, depending on its wavelength.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

Embodiments of the invention will now be described, by way of example, with reference to the accompanying drawings in which:

FIG. 2 illustrates schematically (a) an inspection apparatus adapted to perform angle-resolved scatterometry and dark-field imaging inspection methods in accordance with some embodiments of the invention and (b) an enlarged detail of the diffraction of incident radiation by a target grating in the apparatus of FIG. 2;

FIG. 3 illustrates schematically a pair of wavelength-selective filters used in the apparatus of FIG. 2, with superimposed illustrations of zero order and higher order diffracted radiation;

FIG. 6 depicts a known form of metrology target and an outline of a measurement spot on a substrate;

FIG. 7 depicts an image of the target obtained in a known dark-field imaging method;

FIG. 8 depicts multiple images of the target of FIG. 6 captured using the modified apparatus of FIG. 2;

DETAILED DESCRIPTION

Before describing embodiments of the invention in detail, it is instructive to present an example environment in which embodiments of the present invention may be implemented.

Figure 1:
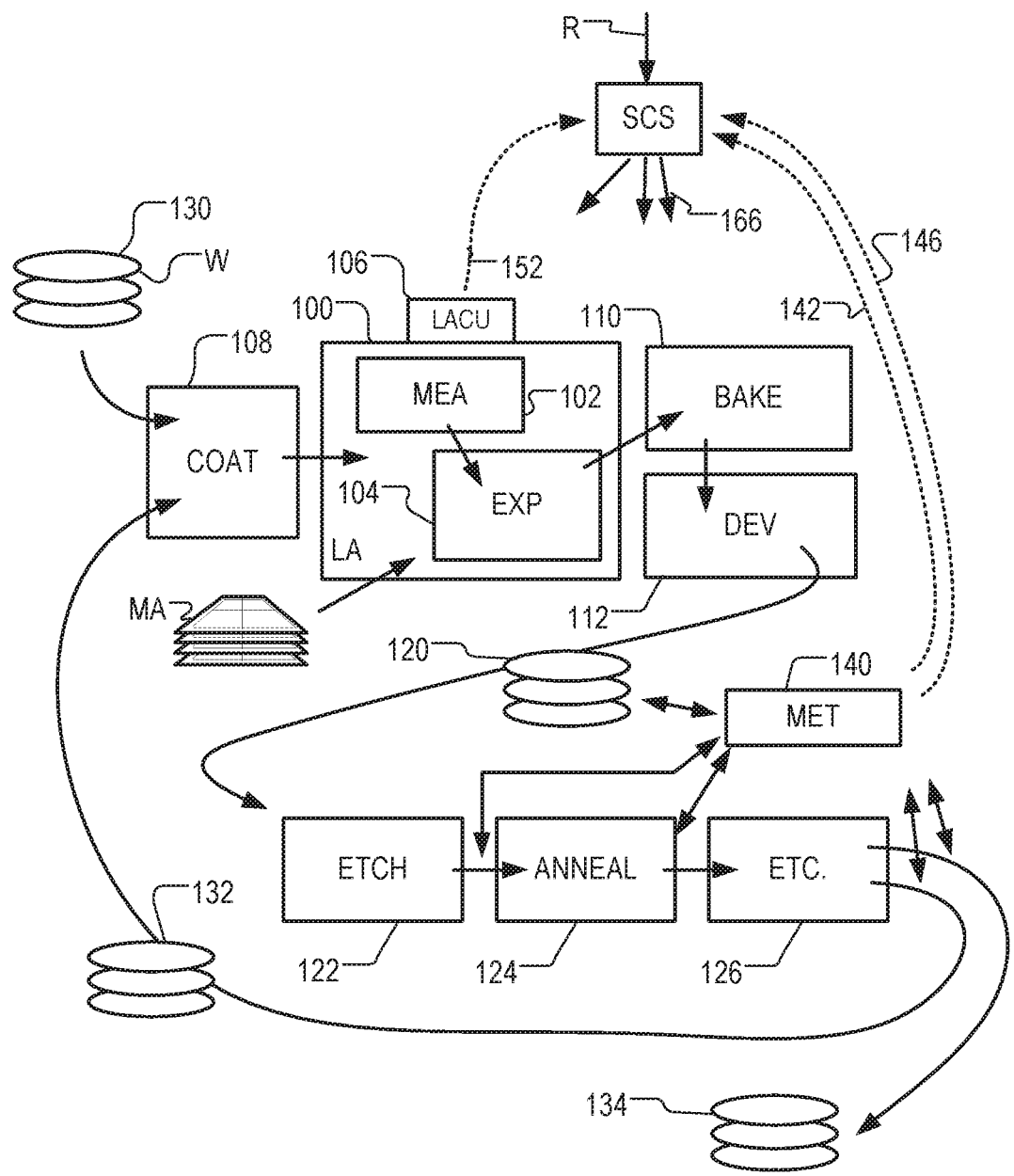
FIG. 1 depicts a lithographic apparatus together with other apparatuses forming a production facility for semiconductor devices.

FIG. 1 at 100 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 100 for short), a measurement station MEA is shown at 102 and an exposure station EXP is shown at 104. A control unit LACU is shown at 106. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU controls the movements and measurements of various actuators and sensors, causing the apparatus LA to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a subsystem or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA for example is of a so-called dual stage type which has two substrate tables WTa and WTb and two stations—an exposure station and a measurement station—between which the substrate tables can be exchanged.

Within the production facility, apparatus 100 forms part of a "litho cell" or "litho cluster" that contains also a coating apparatus 108 for applying photosensitive resist and other coatings to substrates W for patterning by the apparatus 100. At an output side of apparatus 100, a baking apparatus 110 and developing apparatus 112 are provided for developing the exposed pattern into a physical resist pattern. Between all of these apparatuses, substrate handling systems take care of supporting the substrates and transferring them from one piece of apparatus to the next. These apparatuses, which are often collectively referred to as the "track", are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 120 are transferred to other processing apparatuses such as are illustrated at 122, 124, 126. A wide range of processing steps is implemented by various apparatuses in a typical manufacturing facility. For the sake of example, apparatus 122 in this embodiment is an etching station, and apparatus 124 performs a post-etch annealing step. Further physical and/or chemical processing steps are applied in further apparatuses, 126, etc. Numerous types of operation can be required to make a real device, such as deposition of material, modification of surface material characteristics (oxidation, doping, ion implantation etc.), chemical-mechanical polishing (CMP), and so forth. The apparatus 126 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 130 arriving at the litho cluster may be newly prepared substrates, or they may be substrates that have been processed previously in this cluster or in another apparatus entirely. Similarly, depending on the required processing, substrates 132 on leaving apparatus 126 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 126 used at each layer may be completely different in type. Further, even where the processing steps to be applied by the apparatus 126 are nominally the same, in a large facility, there may be several supposedly identical machines working in parallel to perform the step 126 on different substrates. Small differences in set-up or faults between these machines can mean that they influence different substrates in different ways. Even steps that are relatively common to each layer, such as etching (apparatus 122) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located also includes metrology system MET which receives some or all of the substrates W that have been processed in the litho cell. Metrology results are provided directly or indirectly to the supervisory control system (SCS) 138. If errors are detected, adjustments may be made to exposures of subsequent substrates, especially if the metrology can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Also shown in FIG. 1 is a metrology apparatus 140 which is provided for making measurements of parameters of the products at desired stages in the manufacturing process. A common example of a metrology apparatus in a modern lithographic production facility is a scatterometer, for example an angle-resolved scatterometer or a spectroscopic scatterometer, and it may be applied to measure properties of the developed substrates at 120 prior to etching in the apparatus 122. Using metrology apparatus 140, it may be determined, for example, that important performance parameters such as overlay or critical dimension (CD) do not meet specified accuracy requirements in the developed resist. Prior to the etching step, the opportunity exists to strip the developed resist and reprocess the substrates 120 through the litho cluster. As is also well known, the metrology results 142 from the apparatus 140 can be used to maintain accurate performance of the patterning operations in the litho cluster, by supervisory control system SCS and/or control unit LACU 106 making small adjustments over time, thereby minimizing the risk of products being made out-of-specification, and requiring re-work. Of course, metrology apparatus 140 and/or other metrology apparatuses (not shown) can be applied to measure properties of the processed substrates 132, 134, and incoming substrates 130.

Example Inspection Apparatus

FIG. 2(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 2(b).

As described in the prior applications cited in the introduction, the dark-filed-imaging apparatus of FIG. 2(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired.

The objective lens 16 in this example serves also to collect radiation that has been scattered by the target. Schematically, a collection path CP is shown for this returning radiation. The multi-purpose scatterometer may have two or more measurement branches in the collection path. The illustrated example as a pupil imaging branch comprising pupil imaging optical system 18 and pupil image sensor 19. An imaging branch is also shown, which will be described in more detail below. Additionally, further optical systems and branches will be included in a practical apparatus, for example to collect reference radiation for intensity normalization, for coarse imaging of capture targets, for focusing and so forth. Details of these can be found in the prior publications mentioned above.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus. In the case of gratings, the structure is periodic.

The various components of illumination system 12 can be adjustable to implement different metrology 'recipes' within the same apparatus. In addition to selecting wavelength (color) and polarization as characteristics of the illuminating radiation, illumination system 12 can be adjusted to implement different illumination profiles. The plane of aperture device 13 is conjugate with a pupil plane of objective lens 16 and the plane of the pupil image detector 19. Therefore, an illumination profile defined by aperture device 13 defines the angular distribution of light incident on substrate W in spot S. To implement different illumination profiles, an aperture device 13 can be provided in the illumination path. The aperture device may comprise different apertures mounted on a movable slide or wheel. It may alternatively comprise a programmable spatial light modulator. As a further alternative, optical fibers may be disposed at different locations in the illumination pupil plane and used selectively to deliver light or not deliver light at their respective locations. These variants are all discussed and exemplified in the documents cited above.

Depending on the illumination mode, example rays 30a may be provided so that the angle of incidence is as shown at 'I' in FIG. 2(b). The path of the zero order ray reflected by target T is labeled '0' (not to be confused with optical axis 'O'). Similarly, in the same illumination mode or in a second illumination mode, rays 30b can be provided, in which case the angles of incidence and reflection will be swapped compared with the first mode. In FIG. 2(a), the zero order rays of the first and second example illumination modes are labeled 0a and 0b respectively.

As shown in more detail in FIG. 2(b), target grating T as an example of a target structure is placed with substrate W normal to the optical axis O of objective lens 16. In the case of an off-axis illumination profile, a ray 30a of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

In the branch of the collection path for dark-field imaging, imaging optical system 20 forms an image T' of the target on the substrate W on sensor 23 (e.g. a CCD or CMOS sensor). An aperture stop 21 is provided in a plane in the imaging branch of the collection path CP which is conjugate to a pupil plane of objective lens 16. Aperture stop 21 may also be called a pupil stop. Aperture stop 21 can take different forms, just as the illumination aperture can take different forms. The aperture stop 21, in combination with the effective aperture of lens 16, determines what portion of the scattered radiation is used to produce the image on sensor 23. Typically, aperture stop 21 functions to block the zeroth order diffracted beam so that the image of the target formed on sensor 23 is formed only from the first order beam(s). In an example where both first order beams are combined to form an image, this would be the so-called dark field image, equivalent to dark-field microscopy.

The images captured by sensor 23 are output to image processor and controller PU, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose. Special designs of targets are provided to allow these measurements of different performance parameters to be made through the same basic asymmetry measurement method.

Referring again to FIG. 2(b) and the illuminating rays 30a, +1 order diffracted rays from the target grating will enter the objective lens 16 and contribute to the image recorded at sensor 23. Rays 30b are incident at an angle opposite to rays 30a, and so the −1 order diffracted rays enter the objective and contribute to the image. Aperture stop 21 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture stop 21 could be used to pass substantially only one first order of diffracted light to the sensor. In a further example, a pair of off-axis prisms 22 are used in combination with an on-axis illumination mode. These prisms have the effect of diverting the +1 and −1 orders to different locations on sensor 23 so that they can be detected and compared without the need for two sequential image capture steps. In FIG. 2(*a*) for example, an image T'(+1a), made using +1 order diffraction from illuminating ray 30*a*, is spatially separated from an image T'(−1b) made using −1 order diffraction from illuminating ray 30*b*. This technique is disclosed in the above-mentioned published patent application US2011102753A1, the contents of which are hereby incorporated by reference. 2nd, 3rd and higher order beams (not shown in FIG. 2) can be used in measurements, instead of or in addition to the first order beams. As a further variation, the off-axis illumination mode can be kept constant, while the target itself is rotated 180 degrees beneath objective lens 16 to capture images using the opposite diffraction orders.

While a conventional lens-based imaging system is illustrated, the techniques disclosed herein can be applied equally with plenoptic cameras, and also with so-called "lensless" or "digital" imaging systems. There is therefore a large degree of design choice, which parts of the processing system for the diffracted radiation are implemented in the optical domain and which are implemented in the electronic and software domains.

Dual-Wavelength Capture—Principle

FIG. 3 illustrates the use of segmented wavelength-selective filters to allow simultaneous capture of diffraction spectra at two wavelengths in the apparatus of FIG. 2. A first filter 300 is used in place of the aperture device 13 in the illumination optical system of the apparatus. First filter 300 comprises first portions 300-1 having one or more first pass bands in the optical wavelength spectrum, and second portions 300-2 having one or more second pass bands. Such a filter can be fabricated by cutting two filters of different characteristics into segments, and gluing them together in the desired arrangement.

Figure 4:
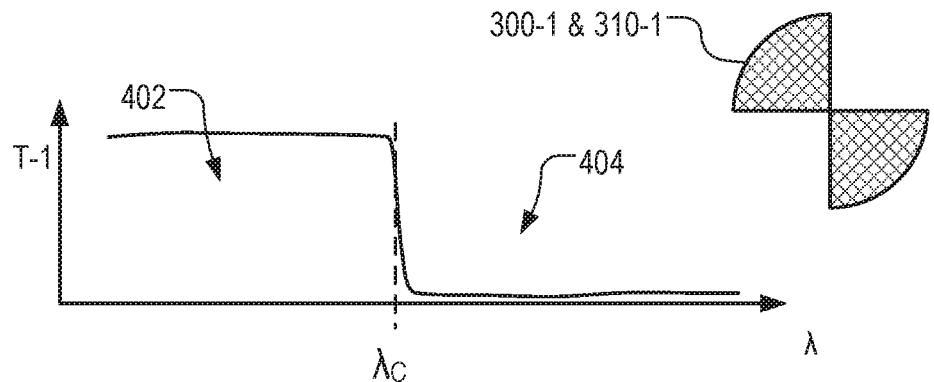
FIG. 4 illustrates spectral transmission characteristics of different portions of the wavelength-selective filters of FIG. 3.
Figure 4:
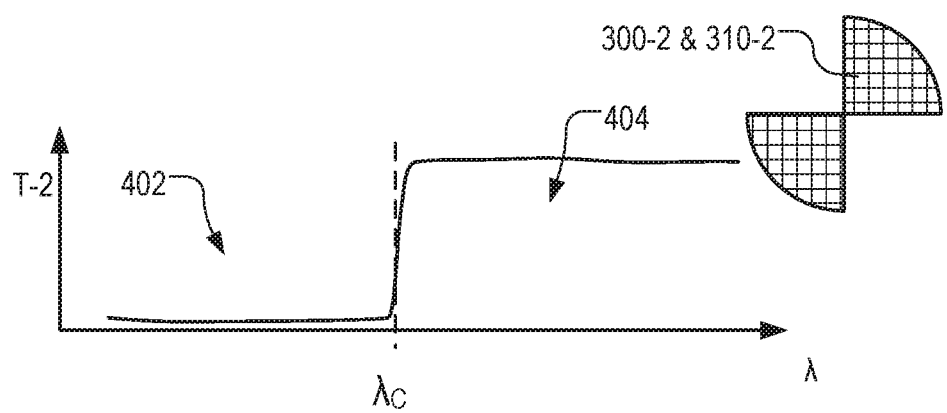

Example transmission spectra of the segmented filter 300 are shown in FIG. 4. Graph T-1 illustrates that first portions 300-1 of the filter 300 have a low pass characteristic in terms of wavelength λ, transmitting radiation having a wavelength in a first wavelength range 402 and blocking radiation having a wavelength in a second wavelength range 404. It will be understood that a low pass characteristic in terms of wavelength is equivalent to a high pass characteristic in terms of frequency or energy. A second graph T-2 illustrates that second portions 300-2 of the filter 300 have a high pass characteristic in terms of wavelength λ. In these portions, radiation having a wavelength in the first wavelength range 402 is blocked, while the radiation in the second wavelength range 404 is transmitted. A cutoff wavelength $\lambda_C$ defines a boundary between the two wavelength ranges. In the present example, the cutoff wavelength is designed to be equal in the two portions. If there were overlap between the pass bands, this would not be a problem for the disclosed technique, provided that radiation having a wavelength within the range of overlap is not used. Similarly, if there were a gap between the pass bands, this would mean only that radiation having a wavelength within that gap cannot be used.

A second filter 310 is used in place of the aperture stop 21. Filter 310 is very similar in form to filter 300, having first portions 310-1 which transmit radiation in the first wavelength range, while blocking radiation in the second wavelength range and having second portions 310-2 which transmit radiation in the second wavelength range while blocking radiation in the first wavelength range. The spectral transmission characteristics of these filter portions are the same as shown in FIG. 4.

Illustrated in FIG. 3 are two example illuminating rays 302 and 304 passing through filter 300. Corresponding positions 302' and 304' are indicated on the drawing of the second filter 310. It will be seen that the second filter 310 is arranged such that its first portions 310-1 lie in portions of the pupil plane diametrically opposite to the second portions 300-2 of the first filter 300, with regard to the optical axis O which passes through the center of the filter. Similarly, second portions 310-2 of the second filter 310 lie in portions of the pupil plane diametrically opposite to the first portions 300-1 of the first filter 300. The zero order reflected rays from illuminating rays 302, 304 arrive at positions 302" and 304" on the second filter 310. No matter the angular position of the illuminating rays passing through first portions of filter 300, the corresponding zero order reflected rays will be blocked by second portions of filter 310. Similarly, no matter the angular position of illuminating rays passing through second portions of filter 300, they will be blocked by first portions of filter 310.

Considering now the first order diffracted radiation scattered by target T (FIG. 2 (*b*)), 302X indicates the position of a diffracted ray from the illuminating ray 302, upon encountering a grating structure that is periodic in the X direction. Similarly, 302Y indicates the position of a diffracted ray from the illuminating ray 302, upon encountering a grating structure that is periodic in the Y direction. Further, 304X and 304Y indicate diffracted rays from the illuminating ray 304. Each of these diffracted rays falls on a portion of the second filter 310 having the same wavelength characteristics as the portion through which the illuminating ray passed in the first filter 300. Accordingly, in the collection optical system of the scatterometer, rays of different wavelengths can be transmitted simultaneously, passing the higher order diffracted rays, and simultaneously blocking the zero order reflected rays for all wavelengths and angular positions.

It will be seen that, with regard to an optical axis of the collection optical system, each segmented wavelength-selective filter 300, 310 has first portions positioned diametrically opposite one another. With regard to a first line of symmetry 320 transverse to a first direction of periodicity of the target structure, for example, the X direction or the Y direction, each segmented wavelength-selective filter 300, 310 has first portions symmetrically opposite second portions. With regard also to a second line of symmetry 322 transverse to a second direction of periodicity of said structure, the segmented wavelength-selective filter again has first portions symmetrically opposite second portions.

The particular segmentation of the filters illustrated in FIG. 3 is based on the segmented illumination aperture described in more detail in US2010201963A1, mentioned above. Instead of simply having transmissive and opaque portions, however, the segmented wavelength-selective filter of the present disclosure has first portions and second portions with complementary transmission spectra. By arranging a second such filter in the collection path CP with appropriate orientation, the benefits of the known segmented aperture can be obtained for two wavelengths simultaneously. Other arrangements of segmentation may be applied, if desired. For example, for some applications it might be sufficient to make a filter of two halves.

Instead of providing the wavelength-selective filters in place of the aperture stop and/or pupil stop, they can be mounted separately, in series with a conventional aperture device and/or field stop. The color filter 12b is another possible location.

Referring again to FIG. 2, it will be seen that radiation source 11 can be implemented by a pair of narrowband radiation sources 11-1 and 11-2 and a common delivery system, such as an optical fiber 11a. First radiation source 11-1 in this example can be tuned to a range of wavelengths in at least a first wavelength range, while second radiation source 11-2 can be tuned to a range of wavelengths in at least a second wavelength range.

Figure 5:
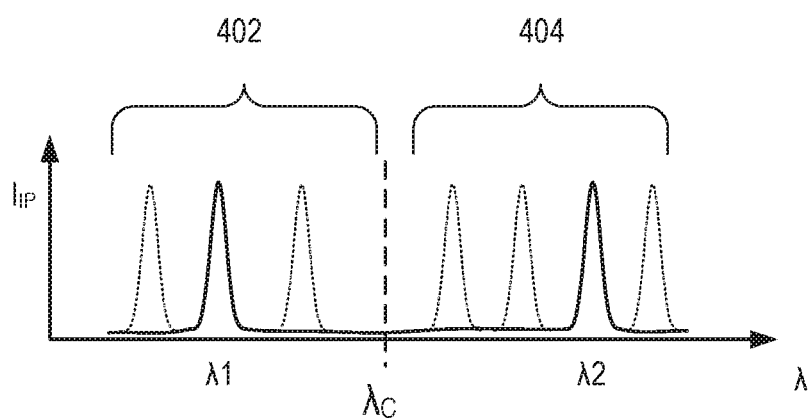
FIG. 5 illustrates use of the filters of FIG. 3 to selectively transmit or block radiation in two different wavebands.

FIG. 5 illustrates example spectral characteristics of the radiation source 11 when two particular wavelengths are selected. First radiation source 11-1 is operating to provide narrowband radiation with a wavelength $\lambda 1$ in the first wavelength range 402. Second radiation source 11-2 is operating to provide narrowband radiation with a wavelength $\lambda 2$ in the second wavelength range 404. Referring again to the arrangement of the segments in the filters 300, 310, and to the spectral characteristics illustrated in FIG. 4, it is arranged that diffracted radiation of both wavelengths can be detected simultaneously and used for metrology purposes, while the zero order radiation of both wavelengths is blocked. More generally, filter 300 therefore has a first pass band in one or more first portions of a pupil plane of said collection optical system and a second pass band in one or more second portions of the pupil plane, the first portions transmitting radiation of the first wavelength while blocking radiation of the second wavelength, the second portions transmitting radiation of the second wavelength while blocking radiation of the first wavelength.

Because the different wavelengths of radiation are separated in the pupil plane, they can be isolated for processing using a four-segmented prism 22, without the loss of transmission that might be associated with the use of frequency selective filters and dual detector arrangement. In principle, the first filter 300 could be omitted, if another suitable way is found to provide illumination of the appropriate angular distribution and wavelength.

As illustrated in FIG. 5, the first wavelength $\lambda 1$ may be one of a number of alternative first wavelengths that can be selected by control of the source 11-1. Similarly, the second wavelength $\lambda 2$ may be one of a number of alternative second wavelengths that can be selected. Depending on the design of the source, discrete wavelengths may be able to be selected, or a continuous tuning may be possible. Suitable sources may be tunable lasers, although a broadband source with a tunable filter could also be used. The bandwidth of the narrowband radiation can be selected to be as broad or narrow as desired, within the pass bands of the filter portions.

Dual-Wavelength Capture—Application Example

An application will now be described, beginning with a description of the principle of the existing small target diffraction-based overlay methods, mentioned in the introduction. The dual-wavelength capture principle is not limited to this particular application, and is not limited to dark-field imaging metrology generally. A second filter 310 can be deployed equally in the first measurement branch, using pupil image sensor 19, as indicated in dotted lines at 21'.

FIG. 6 depicts a composite target formed on a substrate W according to known practice. The composite target comprises four periodic structures in the form of gratings 62 to 65 positioned closely together so that they will all be within the measurement spot S formed by the illumination beam of the metrology apparatus. A circle 61 indicates the extent of spot S on the substrate W. The four gratings thus are all simultaneously illuminated and simultaneously imaged on sensor 23. At the same time, in accordance with the principles of the present disclosure, mentioned above, the four gratings are simultaneously illuminated with at least first and second wavelengths of radiation and simultaneously imaged with both wavelengths of radiation, as will now be explained.

Using only a single wavelength to measure asymmetry, a major contributor to measurement uncertainty in overlay metrology is so-called process dependency. In particular, bottom grating asymmetry influences asymmetry measurements, and not only the overlay or focus performance which is the parameter of interest. One method of correcting for this error is to make multiple measurements with different wavelengths, angles, and/or polarizations. While the actual overlay is insensitive to different properties of light, the bottom grating asymmetry responds differently, and can be compensated by calculations combining asymmetry measured at the various wavelengths. Unfortunately in existing apparatuses, these measurements are done by switching the wavelength filters and this costs a lot of time. By applying the dual-wavelength capture principle illustrated above, the apparatus of FIG. 2 is able to measure asymmetry using two wavelengths of radiation in parallel. The choice of wavelengths can be made and to be free, so as to be tuned to the particular "stack" of multilayers present in the product under inspection.

In an example dedicated to overlay measurement, gratings 62 to 65 are themselves composite gratings formed by overlying gratings that are patterned in different layers of the semi-conductor device formed on substrate W. Gratings 62 to 65 may have differently biased overlay offsets in order to facilitate measurement of overlay between the layers in which the different parts of the composite gratings are formed. Gratings 62 to 65 may also differ in their orientation, as shown, so as to diffract incoming radiation in X and Y directions. In one example, gratings 62 and 64 are X-direction gratings with biases of the +d, −d, respectively. This means that grating 62 has its overlying components arranged so that if they were both printed exactly at their nominal locations one of the components would be offset relative to the other by a distance d. Grating 64 has its components arranged so that if perfectly printed there would be an offset of d but in the opposite direction to the first grating and so on. Gratings 63 and 65 are Y-direction gratings with offsets +d and −d respectively. Separate images of these gratings can be identified in the image captured by sensor 23. While four gratings are illustrated, another embodiment might require a larger matrix to obtain the desired accuracy.

FIG. 7 shows an example of an image that may be formed on and detected by the sensor 23, using the target of FIG. 6 in the apparatus of FIG. 2, and using a conventional illumination profile providing off-axis illumination in both X and Y orientations simultaneously. The dark rectangle 70 represents the field of the image on the sensor, within which the illuminated spot 61 on the substrate is imaged into a corresponding circular area 71. Within this, rectangular areas 72-75 represent the images of the small target gratings 62 to 65. If the gratings are located in product areas, product features may also be visible in the periphery of this image field. Image processor and controller PU processes these images using pattern recognition to identify the separate images 72 to 75 of gratings 62 to 65. In this way, the images do not have to be aligned very precisely at a specific location within the sensor frame, which greatly improves throughput of the measuring apparatus as a whole. However the need for accurate alignment remains if the imaging process is subject to non-uniformities across the image field. In one embodiment of the invention, four positions P1 to P4 are identified and the gratings are aligned as much as possible with these known positions.

Once the separate images of the gratings have been identified, the intensities of those individual images can be measured, e.g., by averaging or summing selected pixel intensity values within the identified areas. Intensities and/or other properties of the images can be compared with one another to obtain measurements of asymmetry for the four or more gratings simultaneously. These results can be combined with knowledge of the target structures and bias schemes, to measure different parameters of the lithographic process. Overlay performance is an important example of such a parameter, and is a measure of the lateral alignment of two lithographic layers. Overlay can be defined more specifically, for example, as the lateral position difference between the center of the top of a bottom grating and the center of the bottom of a corresponding top-grating. To obtain measurements of other parameters of the lithographic process, different target designs can be used. Again, knowledge of the target designs and bias schemes can be combined with asymmetry measurements to obtain measurements of the desired performance parameter. Target designs are known, for example, for obtaining measurements of dose or focus from asymmetry measurements obtained in this way.

In the conventional apparatus, first and second images of the type shown in FIG. 7 are obtained, using selectively the +1 and −1 orders of diffraction. By the use of the prisms 22, both of the +1 and −1 orders of diffraction can be captured at separate regions of the image 70 (not illustrated). Applying the dual-wavelength capture principle of the present disclosure to the small target diffraction based overlay metrology technique just described, FIG. 8 illustrates the image 80 that can be obtained on dark-field image sensor 23 using the complementary segmented filters 300, 310 as the aperture device 13 and aperture stop 21. Instead of a single region 71 corresponding to the extent of illumination spot 61 in FIG. 6, there are now four regions 81. Each corresponds to either a +1 or −1 diffraction order, by the known action of the prismS22 and each corresponds now to a separate wavelength range λ1 or λ2, by action of the segmented wavelength-selected filters, and the prismS22. Within each of the four regions, a corresponding "image" of the composite grating target can be found and isolated for processing. Rectangular areas 82 are labeled. Upright and diagonal hatching are used to distinguish the different wavelength images, using the same hatching convention as in FIG. 3. While the radiation in these different regions has a different color (wavelength), the fact that the regions are spatially separated, allows a monochrome image sensor 23 to be used.

Figure 9:
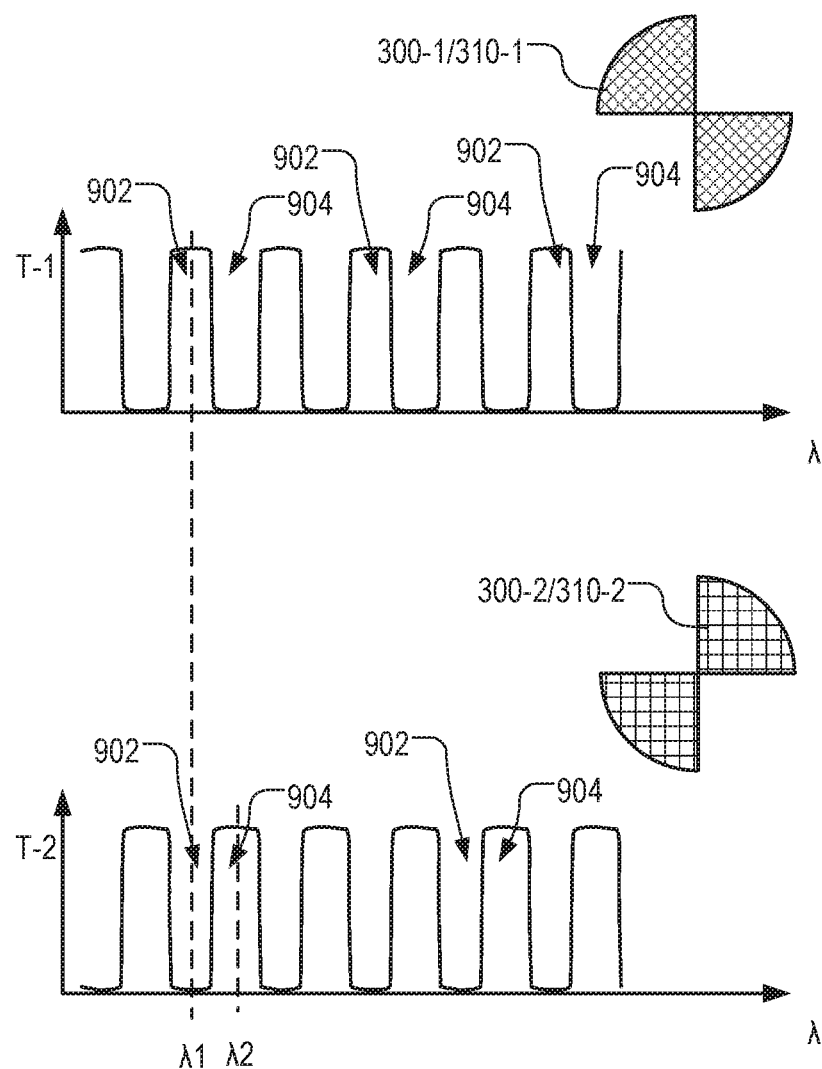
FIG. 9 illustrates spectral transmission characteristics of different portions of the wavelength-selective filters of FIG. 3 in an alternative embodiment.

FIG. 9 illustrates an alternative embodiment in which the first portions and second portions of the segmented wavelength-selected filters 300, 310 have multiple pass bands, instead of a simple high-pass or low-pass characteristic. Instead of only two wavelength ranges 402 and 404, the transmission spectra T-1 and T-2 in this embodiment have multiple first wavelength ranges 902 and multiple second wavelength ranges 904. These transmission spectra may be referred to as "comb" filters. Each passband in the transmission spectrum of the first portions of the filters corresponds with a stop band or "notch" in the transmission spectrum of the second portions. As in the example of FIGS. 4 and 5, a wide range of choices can be made for the first wavelength λ1 and the second wavelength λ2. In contrast to the example of FIGS. 4 and 5, however, the two wavelengths can be now chosen close together as illustrated in FIG. 9. There is no longer a requirement that the first and second wavelengths fall into different halves of the relevant spectrum. Comb filters with suitable characteristics are commercially available. They can be made by appropriately tailored multilayer thin-film structures, or by stacking a number of separate notch filters.

Figure 10:
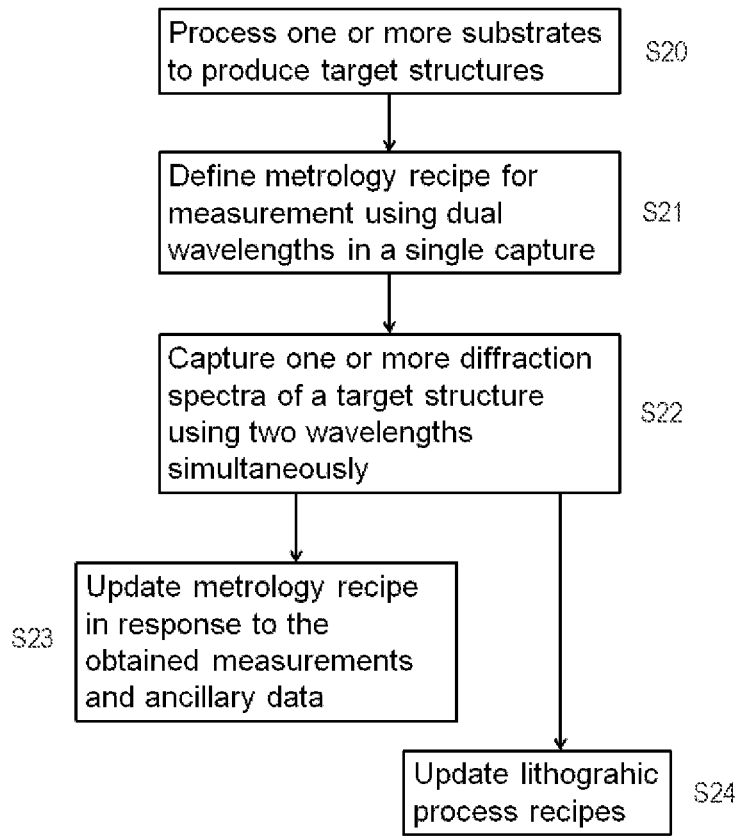
FIG. 10 is a flowchart of a method of measuring corrected measurements of asymmetry using the principles of FIGS. 3 to 8.

FIG. 10 illustrates a method of measuring performance of a lithographic process using the apparatus and methods outlined above. In step S20, one or more substrates are processed to produce target structures such as the composition grating targets illustrated above. The design of target can be any of the known designs, or new designs. Targets may be large target or small target designs, depending whether the first measurement branch or second measurement branch of the apparatus is to be used. Targets may be designed for measurement of overlay, focus or dose through asymmetry. Targets may be designed for measurement of other performance parameters and/or non-asymmetry-related parameters. Linewidth or critical dimension CD is an example of a parameter that may be measured by scatterometry other than through measurement of asymmetry. CD might be measured for example using the first measurement branch and pupil image sensor 19.

In step S21 metrology recipes are defined, including a recipe for measurement using dual wavelengths in a single capture. Wavelengths are selected as described above, so that a first wavelength falls within a passband of only the first portions of the filters 300, 310, and a second wavelength falls within a passband of only the second portions of the filters. All the usual parameters of such a recipe are also defined, including the polarization, angular distribution and so forth.

In step S22, the inspection apparatus of FIG. 2, or other apparatus implementing the principles of the present disclosure, is operated to capture one or more diffraction spectra of a target structure using two wavelengths simultaneously. Properties such as asymmetry are calculated from the captured diffraction spectra of one or more targets. Using the diffraction spectrum of both wavelengths, process dependency is reduced in the asymmetry measurements, leading to more accurate measurements of a performance parameter such as overlay, focus and/or dose.

At step S23, the metrology recipe may be updated in response to the obtained measurements and ancillary data. For example, the metrology techniques for a new product stack may be under development. In step S24, in a development and/or production phase of operating the lithographic production facility of FIG. 1, recipes for the lithographic process may be updated, for example to improve overlay in future substrates.

The calculations to obtain measurements, and to control the selection of wavelengths and other recipe parameters can be performed within the image processor and controller PU of the inspection apparatus. In alternative embodiments, the calculations of asymmetry and other parameters of interest can be performed remotely from the inspection apparatus hardware and controller PU. They may be performed for example in a processor within supervisory control system SCS, or in any computer apparatus that is arranged to receive the measurement data from the controller PU of the inspection apparatus. Control and processing of the calibration measurements can be performed in a processor separate from that which performs high-volume calculations using the correction values obtained. All of these options are a matter of choice for the implementer, and do not alter the principles applied or the benefits obtained.

It is further recognized by the inventors that the filters 300 or 310, as depicted in FIG. 3 for example, provide a filtering effect suitable to illumination with a wavelength bandwidth centered around a fixed value for the wavelength, for which the filter is designed. It would be advantageous if filters 300 or 310 would allow multiple wavelengths to pass through. The scattering process of the illumination beam with the metrology target leads to diffraction orders and the position of the diffraction orders in the detection system is dependent on the wavelength of the illumination beam and also on the periodicity of the metrology target. It is therefore possible that for particular combinations of the periodicity of the metrology target and illumination beam conditions, such as wavelength or polarization, multiple diffraction orders are overlapping on the detector.

Figure 11:
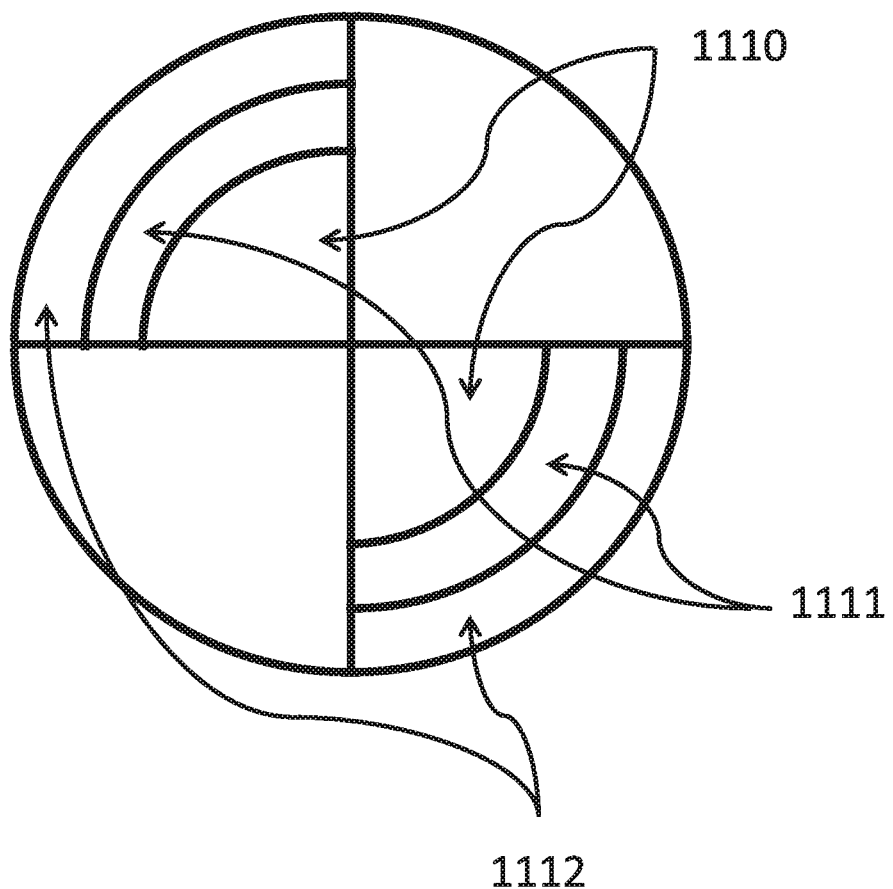
FIG. 11 illustrates an illumination conditions according to an embodiment of the invention.

FIG. 11 illustrates an implementation of filters 300 or 310, implementation which allows multiple wavelength illumination while avoiding diffraction orders overlap, The filters 300 or 310 of FIG. 11 comprise regions 1110, 1111, 1112. Each region functions as a filter for wavelength, allowing a pre-determined wavelength to pass through, wavelength having a bandwidth around the pre-determined wavelength. For example, region 1110 allows shorter wavelengths, in this example between 300 nm and 500 nm, region 1111 allows intermediate wavelengths, in this example, between 500 nm and 600 nm and region 1112 allows longer wavelengths, in this example between 600 nm and 900 nm.

Therefore the invention further provides a wavelength selective filter, the filter being segmented so as to comprise a first and a second portion, each portion being configured to transmit multiple wavelengths.

CONCLUSION

The dual-wavelength capture principle disclosed above allows measurements at two wavelengths to be made simultaneously, to improve overall measurement accuracy without degrading throughput. The technique is suitable for application in asymmetry measurements to be made by dark field imaging methods. Use of two wavelengths provides enhanced accuracy, due to the correction of process dependency effects in the asymmetry signals. The use of small targets allows simultaneous readout of two or more gratings at different positions within the illumination spot, as well as simultaneous readout of diffraction spectra at two wavelengths.

While specific embodiments of the invention have been described above, it will be appreciated that the invention may be practiced otherwise than as described.

While the inspection apparatus or tool illustrated in the embodiments comprises a particular form of scatterometer having first and second branches for simultaneous imaging of pupil plane and substrate plane by parallel image sensors, alternative arrangements are possible. Rather than provide two branches permanently coupled to objective lens 16 with beam splitter 17, the branches could be coupled selectively by a movable optical element such as a mirror. The optical system could be made having a single image sensor, the optical path to the sensor being reconfigured by movable elements to serve as a pupil plane image sensor and then a substrate plane image sensor.

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the inspection apparatus hardware and suitable periodic structures of the targets as realized on substrates and patterning devices, an embodiment may include a computer program containing one or more sequences of machine-readable instructions implementing methods of measurement of the type illustrated above to obtain information about a lithographic process. This computer program may be executed for example within controller PU in the apparatus of FIG. 3 and/or the control unit LACU of FIG. 2. There may also be provided a data storage medium (e.g., semiconductor memory, magnetic or optical disk) having such a computer program stored therein.

Further embodiments according to the present invention are described in below numbered clauses:

1. A method of measuring a property of a structure formed by a lithographic process on a substrate, the method comprising the steps of:
    (a1) illuminating the structure with first radiation having a first wavelength and a first angular distribution;
    (a2) illuminating the structure with second radiation having a second wavelength different to the first wavelength and having a second angular distribution;
    (b1) collecting said first radiation after it has been diffracted by the structure;
    (b2) collecting said second radiation after it has been diffracted by the structure; and
    (c) using one or more portions of the diffracted first radiation and the diffracted second radiation to derive a measurement of said property of the structure,
        wherein the illuminating steps (a1) and (a2) are performed simultaneously, the first angular distribution and the second angular distribution being made different such that the portions of diffracted first radiation that are used in step (c) have an angular distribution that does not overlap with an angular distribution of portions of the diffracted second radiation that are used in step (c), and
        wherein the collecting steps (b1) and (b2) are performed simultaneously using a collection optical system in which a segmented wavelength-selective filter is arranged to transmit the used portions of the diffracted first radiation and of the diffracted second radiation, while simultaneously blocking one or more other portions of the collected first radiation and second radiation that are not used in step (c).

2. A method according to clause 1 wherein the segmented wavelength-selective filter has a first pass band in one or more first portions of a pupil plane of said collection optical system and a second pass band in one or more second portions of the pupil plane, the first portions transmitting radiation of the first wavelength while blocking radiation of the second wavelength, the second portions transmitting radiation of the second wavelength while blocking radiation of the first wavelength.

3. A method according to clause 2 wherein, with regard to an optical axis of said collection optical system, the segmented wavelength-selective filter has first portions positioned diametrically opposite one another.

4. A method according to clause 2 or 3 wherein, with regard to a first line of symmetry transverse to a first direction of periodicity of said structure, the segmented wavelength-selective filter has first portions symmetrically opposite to second portions.

5. A method according to clause 4 wherein, with regard also to a second line of symmetry transverse to a second direction of periodicity of said structure, the segmented wavelength-selective filter has first portions symmetrically opposite to second portions.

6. A method according to any of clauses 2 to 5 wherein said first wavelength is selected from among a plurality of available first wavelengths, all falling within said first pass band.

7. A method according to clause 6 wherein said second wavelength is selected from among a plurality of available second wavelengths, all falling within said second pass band.

8. A method according to any of clauses 2 to 5 wherein the segmented wavelength-selective filter has a plurality of first pass bands in one or more first portions of a pupil plane of said collection optical system and a plurality of second pass bands in one or more second portions of the pupil plane.

9. A method according to any preceding clause wherein the steps (a1) and (a2) are performed using a common illumination optical system, and wherein the common illumination optical system includes a second segmented wavelength-selective filter device, the segmented wavelength-selective filters being oriented such that a zero order ray passing through the illumination optical system and the collection optical system will be blocked by one of said filters or the other, depending on its wavelength.

10. A method according to any preceding clause wherein the measured property is asymmetry and each step (b1) and (b2) comprises:
  (i) forming and detecting a first image of the structure using a first selected portion of diffracted radiation; and
  (ii) forming and detecting a second image of the structure using a second selected portion of the diffracted radiation which is symmetrically opposite to the first part, in a diffraction spectrum of the structure; and
  wherein step (c) includes calculating a measurement of asymmetry in the structure based on intensity values derived from the detected first and second images.

11. A method according to clause 9 wherein to perform steps (b1) (i) and (b2) (i) simultaneously, said first images of the structure using the first radiation and second radiation are formed at spatially separate locations and to perform steps (b1) (ii) and (b2) (ii) simultaneously, said second images of the structure using the first radiation and second radiation wavelengths are formed at spatially separate locations.

12. A method according to clause 10 or 11 wherein in each of steps (b1) and (b2), steps (i) and (ii) are performed simultaneously, forming said first image and second image for each of the different wavelengths at spatially separate locations.

13. A method according to clause 10, 11 or 12 further comprising calculating a performance parameter of said lithographic process based on the asymmetry determined by the method for a plurality of periodic structures.

14. An inspection apparatus configured for measuring a property of a structure on a substrate, the inspection apparatus comprising:
  an illumination optical system operable to illuminate the structure simultaneously with first radiation having a first wavelength and a first angular distribution and with second radiation having a second wavelength different to the first wavelength and having a second angular distribution;
  a collection optical system operable to collect simultaneously said first radiation after it has been diffracted by the structure and to collect said second radiation after it has been diffracted by the structure; and
  a processing system for using one or more portions of the diffracted first radiation and the diffracted second radiation to derive a measurement of said property of the structure,
  wherein the first angular distribution and the second angular distribution are made different such that the portions of diffracted first radiation that are used to derive said measurement have an angular distribution that does not overlap with an angular distribution of portions of the diffracted second radiation that are used to derive said measurement, and
  wherein the collection optical system includes a segmented wavelength-selective filter arranged to transmit the used portions of the diffracted first radiation and of the diffracted second radiation, while simultaneously blocking one or more other portions of the collected first radiation and second radiation that are not used to derive said measurement.

15. An inspection apparatus according to clause 14 wherein the segmented wavelength-selective filter has a first pass band in one or more first portions of a pupil plane of said collection optical system and a second pass band in one or more second portions of the pupil plane, the first portions transmitting radiation of the first wavelength while blocking radiation of the second wavelength, the second portions transmitting radiation of the second wavelength while blocking radiation of the first wavelength.

16. An inspection apparatus according to clause 15 wherein, with regard to an optical axis of said collection optical system, the segmented wavelength-selective filter has first portions positioned diametrically opposite one another.

17. An inspection apparatus according to clause 15 or 16 wherein, with regard to a first line of symmetry transverse to a first direction of periodicity of said structure, the segmented wavelength-selective filter has first portions symmetrically opposite to second portions.

18. An inspection apparatus according to clause 17 wherein, with regard also to a second line of symmetry transverse to a second direction of periodicity of said structure, the segmented wavelength-selective filter has first portions symmetrically opposite to second portions.

19. An inspection apparatus according to any of clauses 14 to 18 wherein the illumination optical system is operable to select said first wavelength from among a plurality of available first wavelengths, all falling within said first pass band.

20. An inspection apparatus according to clause 19 wherein the illumination optical system is operable to select said second wavelength from among a plurality of available second wavelengths, all falling within said second pass band.

21. An inspection apparatus according to any of clauses 15 to 18 wherein the segmented wavelength-selective filter has a plurality of first pass bands in one or more first portions of a pupil plane of said collection optical system and a plurality of second pass bands in one or more second portions of the pupil plane.

22. An inspection apparatus according to any of clauses 14 to 21 wherein the illumination optical system includes a second segmented wavelength-selective filter, the segmented wavelength-selective filters being oriented such that a zero order ray passing through the illumination optical system and the collection optical system will be blocked by one of said filters or the other, depending on its wavelength.

23. An inspection apparatus according to any of clauses 14 to 22 wherein the measured property is asymmetry and wherein the collection optical system is operable for each of said first radiation and second radiation (i) to form and detect a first image of the structure using a first selected portion of diffracted radiation; and (ii) to form and detect a second image of the structure using a second selected portion of the diffracted radiation which is symmetrically opposite to the first part, in a diffraction spectrum of the structure, and the processing system is arranged to calculate a measurement of asymmetry in the structure based on intensity values derived from the detected first and second images.

24. An inspection apparatus according to clause 23 wherein the collection optical system is operable to form said first images using each of the first radiation and second radiation different wavelengths simultaneously at spatially separate locations and to form said second images of the structure using the first radiation and the second radiation simultaneously at spatially separate locations.

25. An inspection apparatus according to clause 23 or 24 wherein the collection optical system is operable to form said first images of the structure using the first radiation and second radiation and said second images of the structure using the first radiation and second radiation, all simultaneously at spatially separate locations.

26. An inspection apparatus according to clause 23, 24 or 25 wherein said processing system is further arranged to calculate a performance parameter of said lithographic process based on asymmetries calculated for a plurality of periodic structures.

27. An inspection apparatus according to clause 26 wherein said processing system is further arranged to calculate a performance parameter of said lithographic process based on asymmetries calculated for a plurality of periodic structures, and wherein the collection optical system is operable to form said first images of the different wavelengths of the plurality of structures and said second images of the different wavelengths, using both the first radiation and the second radiation, all simultaneously at spatially separate locations.

28. A computer program product comprising machine readable instructions for causing a programmable processing device to implement a signal processing part of the processing system of the inspection apparatus according to clause 26 or 27, including extracting said first images and said second images from said spatially separate locations in a detected image.

29. A lithographic system comprising:
a lithographic apparatus comprising:
an illumination optical system arranged to illuminate a pattern;
a projection optical system arranged to project an image of the pattern onto a substrate; and
an inspection apparatus according to clause 26 or 27,
wherein the lithographic apparatus is arranged to use the measurement results from the inspection apparatus, in applying the pattern to further substrates.

30. A method of manufacturing devices wherein a device pattern is applied to a series of substrates using a lithographic process, the method including measuring a property of at least one structure formed as part of or beside said device pattern on at least one of said substrates using a method according to any of clauses 1 to 13, and controlling the lithographic process for later substrates in accordance with the result of the method.

31. A wavelength-selective filter for use in an optical system, the filter being segmented so as to comprise at least first and second portions, the filter having at least a first pass band in one or more first portions and at least a second pass band in one or more second portions, the first portions transmitting radiation of a first wavelength while blocking radiation of a second wavelength, the second portions transmitting radiation of the second wavelength while blocking radiation of the first wavelength.

32. A filter according to clause 31 wherein, with regard to an optical axis of the filter, the segmented wavelength-selective filter has first portions positioned diametrically opposite one another.

33. A filter according to clause 31 or 32 wherein, with regard to a first line of symmetry passing through an optical axis of the filter, the segmented wavelength-selective filter has first portions symmetrically opposite to second portions.

34. A filter according to clause 33 wherein, with regard also to a second line of symmetry passing through said optical axis and perpendicular to the first line of asymmetry, the segmented wavelength-selective filter has first portions symmetrically opposite to second portions.

35. A filter according to any of clauses 31 to 34 wherein the filter has a plurality of first pass bands in said first portions and a plurality of second pass bands in said second portions.

36. A pair of filters each being according to any of clauses 31 to 35 and having identical first pass bands and second pass bands.

37. An inspection apparatus having an illumination optical system for providing illumination using at least two wavelengths of radiation, and a collection optical system for collecting radiation having said two wavelengths after interaction with a target structure, wherein at least one of the illumination optical system and the detection optical system includes a segmented wavelength-selective filter according to any of clauses 31 to 34.

38. An inspection apparatus according to clause 37 wherein each of the illumination optical system and the collection optical system includes a segmented wavelength-selective filter device, the segmented wavelength-selective filters of the two optical systems being oriented such that a zero order ray passing through the illumination optical system and the collection optical system will be blocked by one of said filters or the other, depending on its wavelength.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The breadth and scope of the present invention should not be limited by any of the above-described exemplary embodiments, but should be defined only in accordance with the following claims and their equivalents.

The invention claimed is:

1. A method of measuring a property of a structure formed by a lithographic process on a substrate, the method comprising:
   illuminating the structure with first radiation having a first wavelength and a first angular distribution;
   illuminating the structure with second radiation having a second wavelength different to the first wavelength and having a second angular distribution;
   collecting the first radiation after it has been diffracted by the structure;
   collecting the second radiation after it has been diffracted by the structure; and
   using one or more portions of the diffracted first and second radiation to derive a measurement of the property of the structure,
   wherein the illuminating steps are performed simultaneously, the first and second angular distributions being made different such that the used one or more portions of the diffracted first radiation have an angular distribution that does not overlap with an angular distribution of the used one or more portions of the diffracted second radiation, and
   wherein the collecting steps are performed simultaneously using a collection optical system comprising a segmented wavelength-selective filter configured to transmit the used one or more portions of the diffracted first and second radiation while simultaneously blocking one or more other portions of the collected first and second radiation that are not used in the using step.

2. The method of claim 1, wherein the segmented wavelength-selective filter has a first pass band in one or more first portions of a pupil plane of the collection optical system and a second pass band in one or more second portions of the pupil plane, the one or more first portions of the pupil plane transmitting radiation of the first wavelength while blocking radiation of the second wavelength, the one or more second portions of the pupil plane transmitting radiation of the second wavelength while blocking radiation of the first wavelength.

3. The method of claim 1, wherein:
   the illuminating steps are performed using a common illumination optical system, and
   the common illumination optical system comprises a second segmented wavelength-selective filter device, the segmented wavelength-selective filters being oriented, such that a zero order ray passing through the illumination optical system and the collection optical system will be blocked by one of the filters or the other, depending on its wavelength.

4. The method of claim 1, wherein:
   the property comprises asymmetry;
   each of the collecting steps comprises:
      forming a first image of the structure using a first selected portion of diffracted radiation;
      detecting the first image;
      forming a second image of the structure using a second selected portion of the diffracted radiation which is symmetrically opposite to the first selected portion, in a diffraction spectrum of the structure;
      detecting the second image; and
   the using step comprises determining an asymmetry of the structure based on intensity values derived from each of the respectively detected first and second images.

5. The method of claim 4, further comprising determining a performance parameter of the lithographic process based on asymmetries determined for a plurality of periodic structures.

6. An inspection apparatus configured for measuring a property of a structure on a substrate, the inspection apparatus comprising:
   an illumination optical system configured to illuminate the structure simultaneously with first radiation having a first wavelength and a first angular distribution and with second radiation having a second wavelength different to the first wavelength and having a second angular distribution;
   a collection optical system configured to collect simultaneously the first radiation after it has been diffracted by the structure and the second radiation after it has been diffracted by the structure; and
   a processing system configured to use one or more portions of the diffracted first radiation and the diffracted second radiation to derive a measurement of the property of the structure,
   wherein the first angular distribution and the second angular distribution are made different such that the used one or more portions of the diffracted first radiation have an angular distribution that does not overlap with an angular distribution of the used one or more portions of the diffracted second radiation, and
   wherein the collection optical system comprises a segmented wavelength-selective filter configured to transmit the used one or more portions of the diffracted first radiation and of the diffracted second radiation while simultaneously blocking one or more other portions of the collected first radiation and second radiation that are not used to derive the measurement.

7. The inspection apparatus of claim 6, wherein the segmented wavelength-selective filter has a first pass band in one or more first portions of a pupil plane of the collection optical system and a second pass band in one or more second portions of the pupil plane, the one or more first portions of the pupil plane transmitting radiation of the first wavelength while blocking radiation of the second wavelength, and the one or more second portions of the pupil plane transmitting radiation of the second wavelength while blocking radiation of the first wavelength.

8. The inspection apparatus of claim 6, wherein the illumination optical system comprises a second segmented wavelength-selective filter, the segmented wavelength-selective filters being oriented such that a zero order ray passing through the illumination optical system and the collection optical system will be blocked by one of the filters or the other, depending on its wavelength.

9. The inspection apparatus of claim 6, wherein:
   the measured property comprises asymmetry;
   the collection optical system is configured to:
      form a first image of the structure using a first selected portion of diffracted radiation;
      detect the first image;
      form a second image of the structure using a second selected portion of the diffracted radiation which is symmetrically opposite to the first selected portion, in a diffraction spectrum of the structure, detect the second image; and the processing system configured to determine an asymmetry of the structure based on intensity values derived from the detected first and second images.

10. The inspection apparatus of claim 9, wherein the processing system is further configured to determine a performance parameter of the lithographic process based on asymmetries determined for a plurality of periodic structures.

11. A non-transitory computer program product comprising machine readable instructions for causing a programmable processing device to perform operations comprising:

illuminating the structure with first radiation having a first wavelength and a first angular distribution;

illuminating the structure with second radiation having a second wavelength different to the first wavelength and having a second angular distribution;

collecting the first radiation after it has been diffracted by the structure;

collecting the second radiation after it has been diffracted by the structure; and using one or more portions of the diffracted first and second radiation to derive a measurement of the property of the structure; and extracting first images from the diffracted first radiation and second images from the diffracted second radiation from spatially separate locations in a detected image, wherein the illuminating steps are performed simultaneously, the first and second angular distributions being made different such that the used one or more portions of the diffracted first radiation have an angular distribution that does not overlap with an angular distribution of the used one or more portions of the diffracted second radiation, and wherein the collecting steps are performed simultaneously using a collection optical system comprising a segmented wavelength-selective filter configured to transmit the one or more used portions of the diffracted first and second radiation, while simultaneously blocking one or more other portions of the collected first and second radiation that are not used in the using step.

12. A lithographic system comprising:

a lithographic apparatus comprising:

an illumination source configured to illuminate a pattern;

a projection optical system configured to project an image of the pattern onto a substrate;

an inspection apparatus comprising:

an illumination optical system configured to illuminate a structure simultaneously with first radiation having a first wavelength and a first angular distribution and with second radiation having a second wavelength different to the first wavelength and having a second angular distribution;

a collection optical system configured to collect simultaneously the first radiation after it has been diffracted by the structure and to collect the second radiation after it has been diffracted by the structure; and a processing system configured to use one or more portions of the diffracted first radiation and the diffracted second radiation to derive a measurement of a property of the structure, wherein the first angular distribution and the second angular distribution are made different such that the used one or more portions of the diffracted first radiation have an angular distribution that does not overlap with an angular distribution of the used one or more portions of the diffracted second radiation, and wherein the collection optical system comprises a segmented wavelength-selective filter configured to transmit the used one or more portions of the diffracted first and second radiation while simultaneously blocking one or more other portions of the collected first radiation and second radiation that are not used to derive the measurement, and wherein the lithographic apparatus configured to use the measurement from the inspection apparatus in applying the pattern to further substrates.

13. A method of manufacturing devices where a device pattern is applied to a series of substrates using a lithographic process, the method comprising:

measuring a property of a structure formed as part of or beside the device pattern on at least one of the substrates using a method comprising:

illuminating the structure with first radiation having a first wavelength and a first angular distribution;

illuminating the structure with second radiation having a second wavelength different to the first wavelength and having a second angular distribution;

collecting the first radiation after it has been diffracted by the structure;

collecting the second radiation after it has been diffracted by the structure;

using one or more portions of the diffracted first radiation and the diffracted second radiation to derive a measurement of the property of the structure, and adjusting the lithographic process for subsequent substrates based on the measurement, wherein the illuminating steps are performed simultaneously, the first distribution and second angular distributions being made different such that the used one or more portions of the diffracted first radiation have an angular distribution that does not overlap with an angular distribution of the used one or more portions of the diffracted second radiation, and wherein the collecting steps are performed simultaneously using a collection optical system comprising a segmented wavelength-selective filter configured to transmit the used one or more portions of the diffracted first and second radiation while simultaneously blocking one or more other portions of the collected first radiation and second radiation that are not used in the using step.

* * * * *